(12) United States Patent
Jimenez (10) Patent No.: US 9,301,823 B2
(45) Date of Patent: Apr. 5, 2016

(54) ORAL CARE IMPLEMENT

(75) Inventor: Eduardo J. Jimenez, Manalapan, NJ (US)

(73) Assignee: Colgate-Palmolive Company, New York, NY (US)

( * ) Notice: Subject to any disclaimer, the term of this patent is extended or adjusted under 35 U.S.C. 154(b) by 254 days.

(21) Appl. No.: 13/997,314

(22) PCT Filed: Dec. 23, 2010

(86) PCT No.: PCT/US2010/061955
§ 371 (c)(1),
(2), (4) Date: Jun. 24, 2013

(87) PCT Pub. No.: WO2012/087323
PCT Pub. Date: Jun. 28, 2012

(65) Prior Publication Data
US 2013/0269128 A1 Oct. 17, 2013

(51) Int. Cl.
*A61C 17/34* (2006.01)
(52) U.S. Cl.
CPC ......... *A61C 17/3481* (2013.01); *A61C 2203/00* (2013.01)
(58) Field of Classification Search
CPC .... A46B 5/02; A46B 15/0006; A61C 17/225; A61C 17/3481
See application file for complete search history.

(56) References Cited

U.S. PATENT DOCUMENTS

| | | | |
|---|---|---|---|
| 5,651,157 A | 7/1997 | Hahn | |
| 5,934,968 A | 8/1999 | Lin | |
| 6,920,659 B2 * | 7/2005 | Cacka et al. | 15/22.1 |
| 7,049,790 B2 | 5/2006 | Pfenniger et al. | |
| 7,240,390 B2 | 7/2007 | Pfenniger et al. | |
| 7,409,741 B2 | 8/2008 | Dworzan | |
| 7,713,461 B2 | 5/2010 | Pfenniger et al. | |
| 7,721,371 B2 | 5/2010 | Pfenniger et al. | |
| D652,627 S * | 1/2012 | Nanda | D4/104 |

(Continued)

FOREIGN PATENT DOCUMENTS

| | | |
|---|---|---|
| AU | 650842 | 6/1994 |
| CN | 2394592 | 9/2000 |

(Continued)

OTHER PUBLICATIONS

International Search Report and the Written Opinion of the International Searching Authority issued in International Application PCT/US2010/061955 mailed Oct. 7, 2011.

(Continued)

*Primary Examiner* — Shay Karls (57) ABSTRACT

An oral care implement that rotates about a longitudinal axis. In one aspect, the invention can be an oral care implement comprising: a head; a handle extending along a longitudinal axis and having a flat base surface; a mechanical vibratory device operatively connected to a power source, the mechanical vibratory device comprising an eccentric imparting movement to the head when activated; and wherein the flat base surface is oriented relative to the longitudinal axis of the handle so that the oral care implement can stand in a self-supporting upright orientation on a horizontal flat surface, and wherein when the oral care implement stands in the self-supporting upright orientation and the mechanical vibratory device is activated, the oral care implement rotates about the longitudinal axis while maintaining the self-supporting upright orientation.

23 Claims, 4 Drawing Sheets

(56) References Cited

U.S. PATENT DOCUMENTS

| | | | |
|---|---|---|---|
| D675,448 S * | 2/2013 | Xi et al. | D4/108 |
| 8,966,694 B2 * | 3/2015 | Iwahori et al. | 15/22.1 |
| 2002/0133308 A1 | 9/2002 | Lundell et al. | |
| 2002/0192621 A1 | 12/2002 | Ben-Ari | |
| 2004/0163191 A1 | 8/2004 | Cuffaro et al. | |
| 2006/0057087 A1 | 3/2006 | Moskovich et al. | |
| 2006/0059638 A1 | 3/2006 | Hegemann et al. | |
| 2006/0195995 A1 | 9/2006 | Moskovich et al. | |
| 2006/0236478 A1 | 10/2006 | Hohlbein et al. | |
| 2007/0050931 A1 | 3/2007 | Jimenez et al. | |
| 2008/0010770 A1 | 1/2008 | Hegemann et al. | |
| 2008/0209650 A1 | 9/2008 | Brewer et al. | |
| 2008/0276390 A1 | 11/2008 | Hegemann et al. | |
| 2008/0307594 A1 | 12/2008 | Gatzemeyer et al. | |
| 2009/0007358 A1 | 1/2009 | Hegemann et al. | |
| 2010/0275397 A1 | 11/2010 | Moskovich et al. | |

FOREIGN PATENT DOCUMENTS

| | | |
|---|---|---|
| EP | 0 850 602 | 7/1998 |
| GB | 1 445 019 | 8/1976 |
| JP | 2009268626 | 11/2009 |
| TW | 533853 | 5/2003 |
| WO | WO 2005/007015 | 1/2005 |
| WO | WO 2009/136579 | 11/2009 |

OTHER PUBLICATIONS

Written Opinion of the International Preliminary Examining Authority issued in International Application PCT/US2010/061955 mailed Nov. 26, 2012.

* cited by examiner

ORAL CARE IMPLEMENT

CROSS-REFERENCE TO RELATED PATENT APPLICATIONS

The present application is a U.S. national stage application under 35 U.S.C. §371 of PCT Application No. PCT/US2010/061955, filed Dec. 23, 2010, the entirety of which is incorporated herein by reference.

FIELD OF THE INVENTION

The present invention relates generally to an oral care implement having a base that enables the oral care implement to be stood in self-supporting upright orientation and rotate upon activation of a mechanical vibratory device.

BACKGROUND OF THE INVENTION

Powered toothbrushes and other oral care implements have been designed and improved upon for many years. Powered toothbrushes are designed to assist a user in cleaning his or her teeth by creating movement or vibration in the head of the toothbrush. With a powered toothbrush, a user needs to only gently move the toothbrush head across the user's teeth and the mechanical vibration or movement in the head will automatically perform a cleaning and scrubbing action to the teeth. Powered toothbrushes can be beneficial for children and older adults who do not have sufficient coordination, strength and control to effectively clean their teeth manually.

It is often difficult to convince a child to brush his or her teeth because children find the act of brushing their teeth to be dull and children do not fully understand the benefits. Children typically respond well to entertainment, and are more inclined to perform an activity if they perceive the activity as being fun and entertaining. Furthermore, despite the fact that powered toothbrushes may assist a child with ensuring an effective cleaning of the teeth, children may be afraid to use powered toothbrushes because powered toothbrushes may generate noise. Further still, powered toothbrushes produce a vibration that can be felt by the user's hand on the handle. Children and adults alike may find the vibrations uncomfortable and may therefore refrain from using powered oral care implements despite their beneficial qualities.

Thus, a need exists for a powered toothbrush that has the ability to entertain the user in order to make the act of brushing one's teeth more fun and/or to negate any negative associations that a child or adult may have with powered toothbrushes.

BRIEF SUMMARY OF THE INVENTION

Embodiments of the present invention provide an oral care implement, more particularly a powered oral care implement that combines cleaning efficiency with entertainment. Advantageously, the oral care implement is easily portable and sized so that it can be readily gripped by adults and children alike. The oral care implement is capable of standing in a self-supporting upright orientation on a substantially flat surface. Further, the oral care implement has a handle having a longitudinal axis. The oral care implement rotates about the longitudinal axis when a mechanical vibratory device positioned within the oral care implement is activated while maintaining the self-supporting upright orientation, thereby giving the appearance of dancing and/or twirling.

In one aspect, the invention can be an oral care implement comprising: a head; a handle extending along a longitudinal axis, a proximal end of the handle comprising a flat base surface; a mechanical vibratory device operatively connected to an electric power source, the mechanical vibratory device comprising an eccentric that imparts vibration to the head when the mechanical vibratory device is activated; and wherein the flat base surface is oriented relative to the longitudinal axis of the handle so that the oral care implement can stand in a self-supporting upright orientation on a substantially horizontal flat surface, and wherein when the oral care implement stands in the self-supporting upright orientation and the mechanical vibratory device is activated, the oral care implement rotates about the longitudinal axis while maintaining the self-supporting upright orientation.

In another aspect, the invention can be an oral care implement comprising: a head; a handle extending along a longitudinal axis and having a flat base surface; a mechanical vibratory device operatively connected to an electric power source, the mechanical vibratory device comprising an eccentric that imparts movement to the head when the mechanical vibratory device is activated; and wherein the flat base surface is oriented relative to the longitudinal axis of the handle so that the oral care implement can stand in a self-supporting upright orientation on a substantially horizontal flat surface, and wherein when the oral care implement stands in the self-supporting upright orientation and the mechanical vibratory device is activated, the oral care implement rotates about the longitudinal axis while maintaining the self-supporting upright orientation.

In a further aspect, the invention can be an oral care implement comprising: a head; a handle extending along a longitudinal axis, a proximal end of the handle comprising a flat base surface; a neck connecting the head to a distal end of the handle, the neck extending along a longitudinal axis that is inclined relative to the longitudinal axis of the handle; a mechanical vibratory device located in the neck and operatively connected to an electric power source located in the handle, the mechanical vibratory device comprising an eccentric that imparts vibration to the head when the mechanical vibratory device is activated; and wherein the flat base surface is oriented relative to the longitudinal axis of the handle so that the oral care implement can stand in a self-supporting upright orientation on a substantially horizontal flat surface.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The features of the exemplified embodiments will be described with reference to the following drawings in which like elements are labeled similarly. The present invention will become more fully understood from the detailed description and the accompanying drawings, wherein.

DETAILED DESCRIPTION OF THE INVENTION

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "left," "right," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

Exemplary embodiments of the present invention will now be described with respect to one possible oral care system. While the invention will be described herein below with respect to the use of a toothbrush and more specifically a powered toothbrush, it is to be understood that other alternate oral care implements can be used within the scope of the invention, including tongue cleaners, tooth polishers, flossing devices, and other ansate oral care implements.

Figure 1:
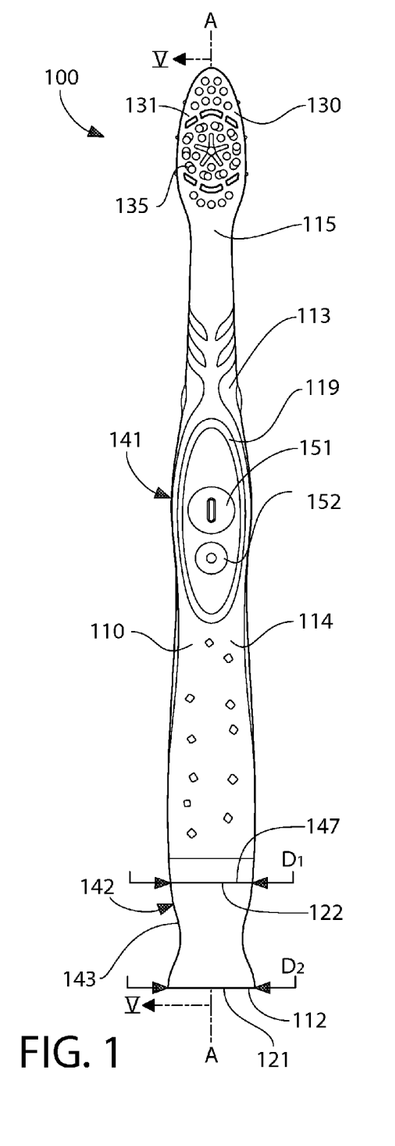
FIG. 1 is a front view of an oral care implement in accordance with an embodiment of the present invention.
Figure 2:
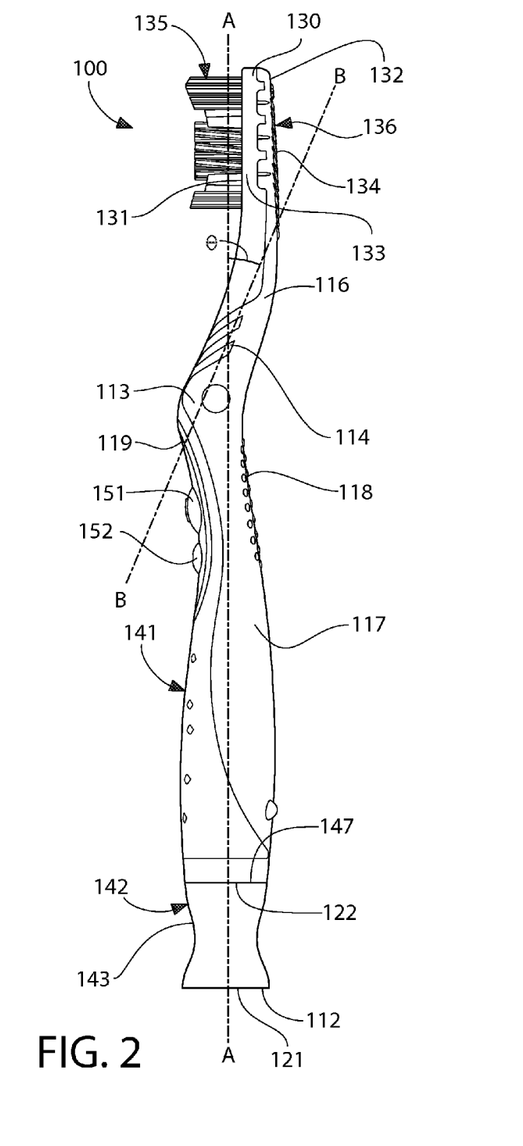
FIG. 2 is a side view of the oral care implement of FIG. 1.
Figure 3:
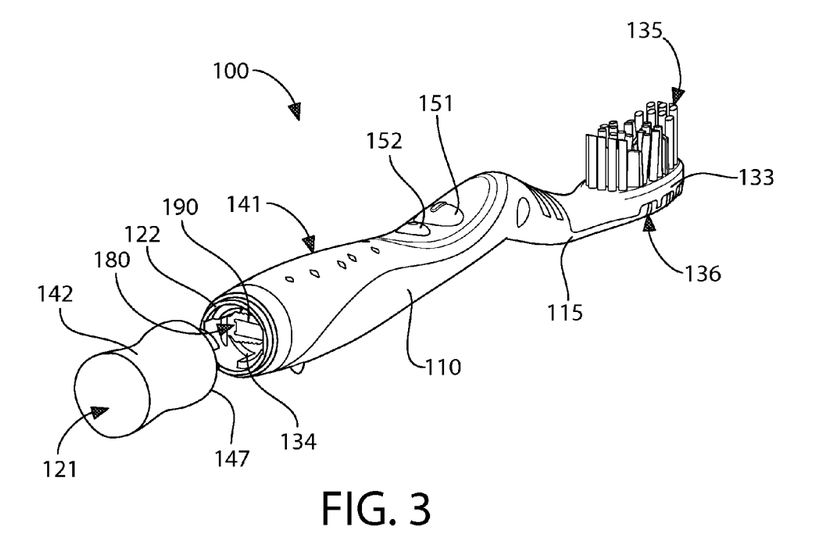
FIG. 3 is a bottom perspective view of the oral care implement of FIG. 1 with a base portion removed from a gripping portion.

Referring to FIGS. 1-3 concurrently, a toothbrush 100 in accordance with an embodiment of the present invention is illustrated. The toothbrush 100 generally comprises a handle 110, a neck 115 and a head 130. The neck 115 extends between the handle 110 and the head 130 and connects the head 130 to a distal end 113 of the handle 110. The handle 110 provides the user with a mechanism by which he/she can readily grip and manipulate the toothbrush 100. The handle 110 may be formed of many different shapes, sizes and materials and may be formed by a variety of manufacturing methods that are well-known to those skilled in the art. The handle 110 can be a single or multi-part construction. The handle 110 extends from a proximal end 112 to the distal end 113 along a longitudinal axis A-A.

The proximal end 112 of the handle 110 comprises a flat base surface 121. In the exemplified embodiment, the flat base surface 121 is substantially perpendicular to the longitudinal axis A-A so that the toothbrush 100 can be positioned in a self-supporting upright orientation on a substantially horizontal flat surface as will be described in more detail below. However, in certain other embodiments, the flat base surface 121 may be inclined elative to the longitudinal axis A-A. Whether the flat base surface 121 is substantially perpendicular to or inclined relative to the longitudinal axis A-A will depend on the location of the center of gravity of the toothbrush 100. In accordance with the present invention, the flat base surface 121 is oriented relative to the longitudinal axis A-A so that when the toothbrush 100 is positioned atop a substantially horizontal flat surface and supported by the flat base surface 121, the center of gravity of the toothbrush is located within the perimeter of the flat base surface 121. In this manner, the toothbrush 100 can stand in a self-supporting upright orientation.

In certain embodiments, the handle 110 can be conceptually or physically separated into an elongated gripping portion 141 and a base portion 142. In certain such embodiments, the base portion 142 can be detachably (i.e., removably) coupled to a bottom end 122 of the elongated gripping portion 141. The base portion 142, whether detachable or not, comprises the flat base surface 121. The base portion 142 may be coupled to the elongated gripping portion 141 by any means known in the art, such as a tight-fit assembly, an interference fit, a snap fit, a coupling sleeve, threaded engagement, adhesion or fasteners. The base portion 142 attaches to the elongated gripping portion 141 in a seamless manner so that the combined base portion 142 and gripping portion 141 form a continuous outer surface of handle 110. Such a seamless connection results in the toothbrush 100 being more attractive to a consumer and may also result in the handle 100 being more comfortable to control during use. However, it is understood that such a continuous outer surface of the handle 110 may not be present in certain embodiments.

In the exemplified embodiment, the base portion 142 comprises a waist 143. The waist 143 is a section of the base portion 142 that has a reduced transverse cross-sectional area relative to the remainder of the base portion 142. Thus, the base portion 142 tapers inwardly from a top surface 147 to the waist 143 and also from the flat bottom surface 121 to the waist 143. In other words, the waist 143 has a transverse cross-sectional area that is less than a transverse cross-sectional area of the flat base surface 121 and the top surface 147 of the base portion 142 (and of the elongated gripping portion 141). Thus, in the exemplified embodiment, the base portion 142 takes on an hourglass shape. Of course, the invention is not so limited and the base portion 142 may take on other known shapes and configurations so long as the base portion 142 has a flat base surface 121 and is able to maintain the toothbrush 100 in a self-supporting upright orientation. In certain embodiments, grooves and/or indentation may be formed in the flat base surface 121, so long as they do not affect the ability of the toothbrush 100 to be stood in the self-supporting upright orientation described above.

Figure 4:
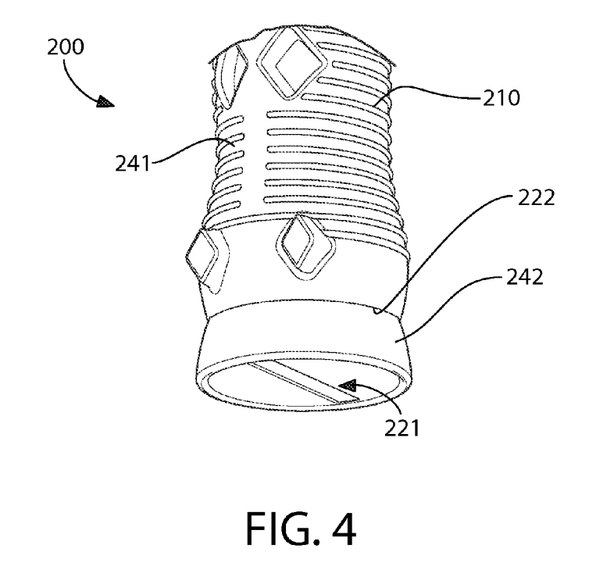
FIG. 4 is a close-up perspective view of a bottom portion of a handle of an oral care implement in accordance with a second embodiment of the present invention.

Referring to FIG. 4, an alternative embodiment of a portion of a toothbrush 200 having a base portion 242 is illustrated. Similarly to the toothbrush 100, the base portion 242 of the toothbrush 200 is detachably coupled to a bottom end 222 of an elongated gripping portion 241 of a handle 210. In FIG. 4, the base portion 242 comprises a tapered shape such that it tapers inwardly from the base surface 221 towards the bottom end 222 of the elongated gripping portion 241. The embodiment illustrated in FIG. 4 is only one alternative embodiment of the base portion and the shape and configuration of the base portion 242 is not to be limiting of the present invention unless specifically recited in a claim.

Referring again to FIGS. 1-3, the base surface 121 of the base portion 142 has a first diameter $D_1$. The bottom end 122 of the elongated gripping portion 141 of the handle 110 has a second diameter $D_2$. In the exemplified embodiment, the second diameter $D_2$ is substantially equal to the first diameter $D_1$. However, the second diameter $D_2$ may be slightly larger or slightly smaller than the first diameter $D_1$ in certain other embodiment. For example, the second diameter $D_2$ may be between about 5% and about 20% smaller or larger than the first diameter $D_1$.

If desired, the handle 110 may include a suitable textured grip 114 made of a soft elastomeric material. In the exemplary embodiment, the textured grip 114 covers a rear surface 116 of the neck 115 and extends to a rear surface 132 of the head 130 and to at least a portion of a rear surface 117 of the handle 110, the details of which will be described in greater detail below. Furthermore a portion of a front surface 119 of the handle 110 is also formed of or covered with a soft elastomeric material.

In embodiments where the textured grip 114 extends to the rear surface 132 of the head 130, the textured grip 114 on the rear surface 132 of the head 130 may act as a soft tissue cleaner 136 or a tooth polishing structure for oral cleaning or tooth engagement. In the exemplary embodiment, the rear surface 132 comprises the soft tissue cleaner 136, which is illustrated as being an elastomeric pad comprising a plurality of nubs and/or ridges 134 extending therefrom. An example of a tooth polishing structure that could be used in place of the soft tissue cleaner 136 is an elastomeric element, such as a prophy cup(s) or elastomeric wipers.

Furthermore, the portion of the textured grip 114 located on the rear surface 117 of the handle 110 comprises a plurality of nubs 118 protruding outwardly therefrom to serve as a thumb or forefinger grip for added comfort and control during toothbrushing. The textured grip 114 is illustrated as being continuous from the rear surface 132 of the head 130 to the proximal end 112 of the handle 110. Of course, the invention is not so limited and the textured grip 114 may be non-continuous in certain other embodiments or omitted all together. In certain other embodiments, the oral care implement 100 may include the soft tissue cleaner 136 while the textured grip 114 does not extend to the handle 110 to act as a grip and vice versa.

As discussed above, a portion of the front surface 119 of the handle 110 is also covered by or formed from the material of the textured grip 114. This portion of the textured grip 114 comprises a switch, which comprises an "on" button 151 and an "off" button 152 for alternating an internal electrical switch between an open and closed state, which in turn provides or cuts off electric power to a mechanical vibratory device 170 (described in greater detail below with reference to FIGS. 5 and 6). The "on" button 151 and the "off" button 152 are minor protrusions in the front surface 119 of the handle 110 that extend outwardly from the front surface 119 of the handle 110 for easy manipulation and depressing by a user. Specifically, when a user holds the toothbrush 100 in a normal fashion, the user's thumb will be positioned adjacent the "on" and "off" buttons 151, 152 to easily enable the user to activate and deactivate the mechanical vibratory device 170 as desired. Of course, the invention is not so limited and the "on" and "off" buttons 151, 152 may be otherwise located on the handle 110, the neck 115 or elsewhere on the toothbrush 100 as would be understood by persons skilled in the art. By forming the "on" and "off" buttons 151, 152 out of the soft thermoplastic elastomer material of the textured grip 114, the "on" and "off" buttons 151, 152 readily deform for manipulation of the switch in response to pressure by a user.

Of course, other types of switches may be used in conjunction with the toothbrush 100 for activating and deactivating the mechanical vibratory device 170, including without limitation slide switches, toggle switches, motion activated switches, photo-sensitive switches, sound-activated switches, electronic switches, and/or combinations thereof.

The handle 110 transitions into the neck 115 at the distal end 113 of the handle 110. While the head 130 is normally widened relative to the neck 115, in some constructions the head 130 can simply be a continuous extension or narrowing of the neck 115 and/or handle 110. While the neck 115 generally has a smaller transverse cross-sectional area than the handle 110, the invention is not so limited. Broadly speaking, the neck 115 is the conceptual transition region between the handle 110 and the head 130. However, in the exemplified embodiment, the neck 115 also serves as a housing for the mechanical vibratory device 170 (FIG. 5), which will be described in greater detail below.

The neck 115 extends along a longitudinal axis B-B that is inclined at a non-zero angle θ relative to the longitudinal axis A-A of the handle 110. The angle θ is an acute angle in the exemplified embodiment. In certain embodiments, the angle θ is preferably an acute angle between about 10° and about 60°, more preferably an acute angle between about 15° and about 40°, and most preferably an acute angle between about 20° and about 30°. The head 130 extends from an end of the neck 115 opposite the handle 110 and in a direction that is generally parallel to the longitudinal axis A-A. However, due to the inclination of the longitudinal axis B-B relative to the longitudinal axis A-A, the head 130 is offset from the longitudinal axis A-A of the handle 110.

In the exemplified embodiment, the head 130, the handle 110, and the neck 115 of the toothbrush 100 are formed as a single unitary structure using a molding, milling, machining or other suitable process. However, in other embodiments, the handle 110, the neck 115 and the head 130 may be formed as separate components which are operably connected at a later stage of the manufacturing process by any suitable technique known in the art, including without limitation thermal or ultrasonic welding, a tight-fit assembly, a coupling sleeve, threaded engagement, adhesion, or fasteners. Whether the head 130, the handle 110, and the neck 115 are of a unitary or multi-piece construction (including connection techniques) is not limiting of the present invention, unless specifically set forth in a claim. In some embodiments of the invention, the head 130 may be detachable (and replaceable) from the handle 110 and/or from the neck 115 using techniques known in the art.

The head 130 generally comprises a front surface 131, a rear surface 132 and a peripheral side surface 133 that extends between the front and rear surfaces 131, 132. The front surface 131 and the rear surface 132 of the head 130 can take on a wide variety of shapes and contours, none of which are limiting of the present invention. For example, the front and rear surfaces 131, 132 can be planar, contoured or combinations thereof.

The front surface 131 of the head 130 comprises a collection of oral cleaning elements, such as tooth engaging elements 135, extending therefrom for cleaning and/or polishing contact with an oral surface and/or interdental spaces. While the collection of tooth engaging elements 135 is suited for brushing teeth, the collection of tooth engaging elements 135 can also be used to polish teeth instead of or in addition to cleaning teeth. As used herein, the term "tooth engaging elements" is used in a generic sense to refer to any structure that can be used to clean, polish or wipe the teeth and/or soft oral tissue (e.g. tongue, cheek, gums, etc.) through relative surface contact. Common examples of "tooth engaging elements" include, without limitation, bristle tufts, filament bristles, fiber bristles, nylon bristles, spiral bristles, rubber bristles, elastomeric protrusions, flexible polymer protrusions, combinations thereof and/or structures containing such materials or combinations. Suitable elastomeric materials include any biocompatible resilient material suitable for uses in an oral hygiene apparatus. To provide optimum comfort as well as cleaning benefits, the elastomeric material of the tooth or soft tissue engaging elements has a hardness property in the range of A8 to A25 Shore hardness. One suitable elastomeric material is styrene-ethylene/butylene-styrene block copolymer (SEBS) manufactured by GLS Corporation. Nevertheless, SEBS material from other manufacturers or other materials within and outside the noted hardness range could be used.

The tooth engaging elements 135 of the present invention can be connected to the head 130 in any manner known in the art. For example, staples/anchors, in-mold tufting (IMT) or anchor free tufting (AFT) could be used to mount the cleaning elements/tooth engaging elements. In AFT, a plate or membrane is secured to the brush head such as by ultrasonic welding. The bristles extend through the plate or membrane. The free ends of the bristles on one side of the plate or membrane perform the cleaning function. The ends of the bristles on the other side of the plate or membrane are melted together by heat to be anchored in place. Any suitable form of cleaning elements may be used in the broad practice of this invention. Alternatively, the bristles could be mounted to tuft blocks or sections by extending through suitable openings in the tuft blocks so that the base of the bristles is mounted within or below the tuft block.

Referring solely now to FIG. 3, the handle 110 is a housing for containing an electric power source 190. Specifically, the handle 100 is a hollow tubular structure having a cavity 180 formed therein. More specifically, in the exemplified embodiment, the cavity 180 is formed in the elongated gripping portion 141 of the handle 110. In the exemplified embodiment, the electric power source 190 is a single AAA battery located within the handle 110. Of course, the invention is not so limited and more or less than one AAA battery may be used or other electric power elements or power sources may be used. An opening 134 is provided at the bottom end 122 of the elongated gripping portion 141 of the handle 110 that provides a passageway into the cavity 180 through which the electric power source 190 can be inserted and retracted. While the opening 134 is located near the proximal end 112 of the handle 110 in the exemplified embodiment, the opening 134 may be located at other positions on the handle 110 in other embodiments of the invention. For example, the opening 134 may be located on a longitudinal surface of the handle 110 (e.g., the front surface, the rear surface and/or the side surfaces) and be elongated to provide sufficient access to the cavity 180.

During use, a user slides the electric power source 190 through the opening 134 and into the cavity 180 in the elongated gripping portion 141 of the handle 100. The user then couples the base portion 142 to the bottom end 122 of the elongated gripping portion 141 of the handle 110. In the exemplified embodiment, the base portion 142 attaches to the bottom end 122 of the elongated gripping portion 141 through a threaded engagement. Thus, the base portion 142 is merely screwed onto the elongated gripping portion 141 by aligning the threads of the base portion 142 with the threads of the bottom end 122 of the elongated gripping portion 141. However, any of the attachment methods discussed above may be used in the alternative.

Figure 5:
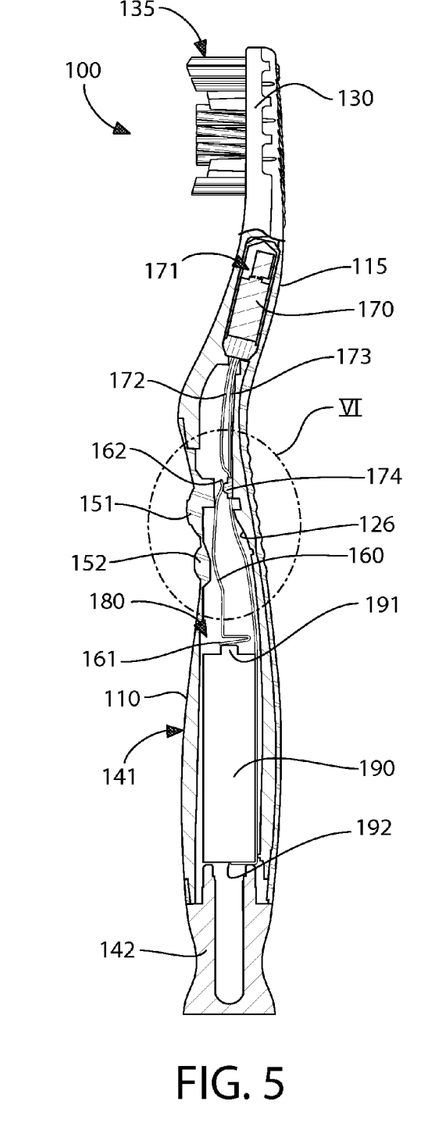
FIG. 5 is a cross-sectional view taken along line V-V of FIG. 1.
Figure 6:
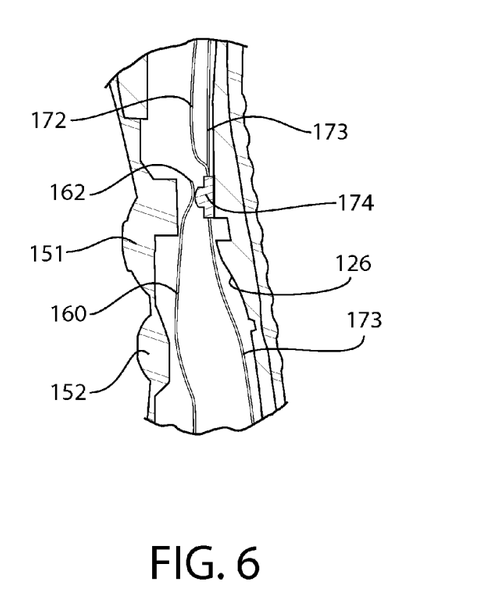
FIG. 6 is a close-up view of area VI of FIG. 5.

Referring now to FIGS. 5 and 6 concurrently, the internal components of the toothbrush 100 will be described in more detail. As discussed above, an electric power source 190, such as a battery, is housed within the cavity 180 of the handle 110. The electric power source 190 has a positive pole 191 and a negative pole 192.

In exemplified embodiment, the mechanical vibratory device 170 is positioned within a cavity 171 formed in the neck 115. The mechanical vibratory device 170 imparts vibrational movement to the head 130 when the mechanical vibratory device 170 is activated. In one specific embodiment, the mechanical vibratory device 170 generates vibrations that are transmitted through the neck 115 and to the head 130. In the exemplified embodiment, the tooth cleaning elements 135 are bristles that are mounted and secured to the head 130. Thus, when the mechanical vibratory device 170 transmits the vibrations to the head 130, the tooth cleaning elements 135 also vibrate. In the exemplary embodiment, the tooth cleaning elements 135 do not rotate, nor are they mounted in a bristle block that moves back and forth relative to the head 130. The tooth cleaning elements 135 merely vibrate by nature of being mounted and secured to the head 130, which receives vibrations from the mechanical vibratory device 170 via the neck 115. Of course, the invention is not so limited and in certain other embodiments, the tooth cleaning elements 135 may be mounted on a movable bristle block or the tooth cleaning elements 135 may be caused to rotate instead of or in addition to the vibratory movement.

The mechanical vibratory device 170 comprises an eccentric (not illustrated) which creates the vibrational movement. The mechanical vibratory device 170 may include a motor, a shaft and an eccentric cam, to provide vibration or movement to the head 130. The mechanical vibratory device 170 is positioned in the neck 115, which as discussed above, is inclined or angled relative to the longitudinal axis A-A of the handle 110. Thus, the mechanical vibratory device 170 is positioned within the neck 115 so as to be inclined relative to the longitudinal axis A-A of the handle 110. As a result, the mechanical vibratory device 170 is offset relative to the longitudinal axis A-A. More specifically, the mechanical vibratory device 170 is positioned within the cavity 171 in the neck 115 so that the eccentric of the mechanical vibratory device 170 is offset relative to the longitudinal axis A-A of the handle 110.

The mechanical vibratory device 170 is coupled to two electric lead wires 172, 173. The electric lead wire 173 extends from the mechanical vibratory device 170 directly to the negative pole 192 of the electric power source 190. In certain embodiments, the electric lead wire 173 is not directly connected to the electric power source 190. In such embodiments, the base portion 142 comprises a metal contact (not illustrated) that abuts both the electric lead wire 173 and the negative pole 192 of the electric power source 190, thereby indirectly connecting the electric lead wire 173 to the negative pole 192. In other words, the base portion 142 may be used to bridge a gap between the electric lead wire 173 and the negative pole 192 of the electric power source 190, thereby closing the circuit.

The electric lead wire 172 extends from the mechanical vibratory device 170 to a switching contact 174. The switching contact 174 is a small piece of metal or other electrically conducting material that is embedded in and extends upwardly from an inner surface 126 of the handle 110. The positive pole 191 of the electric power source 190 abuts against and is operably coupled to a first end 161 of a switch 160. A second end 162 of the switch 160 abuts against and is operably coupled to the switching contact 174. Thus, in the configuration illustrated, the switch 160 is in the "on" position such that the electric power source 190 is operatively connected to the mechanical vibratory device 170 so that the mechanical vibratory device 170 becomes activated and imparts vibration to the head 130.

However, the switch 160 can be changed from the "on" position to an "off" position simply by pressing down on the "off" button 152. Pressing down on the "off" button 152 will cause the second end 162 of the switch 160 to become disengaged from the switching contact 174 so that mechanical vibratory device 170 is no longer operatively connected to the electric power source 190. Thus, when the "off" button 152 is depressed, the mechanical vibratory device 170 will not impart vibration to the head 130. The switch 160 can be turned back to the "on" position by depressing the "on" button 151. In other words, the switch 160 is configured for activating and deactivating the mechanical vibratory device 170 upon depressing of the "on" button 151 and the "off" button 152, respectively.

Figure 7:
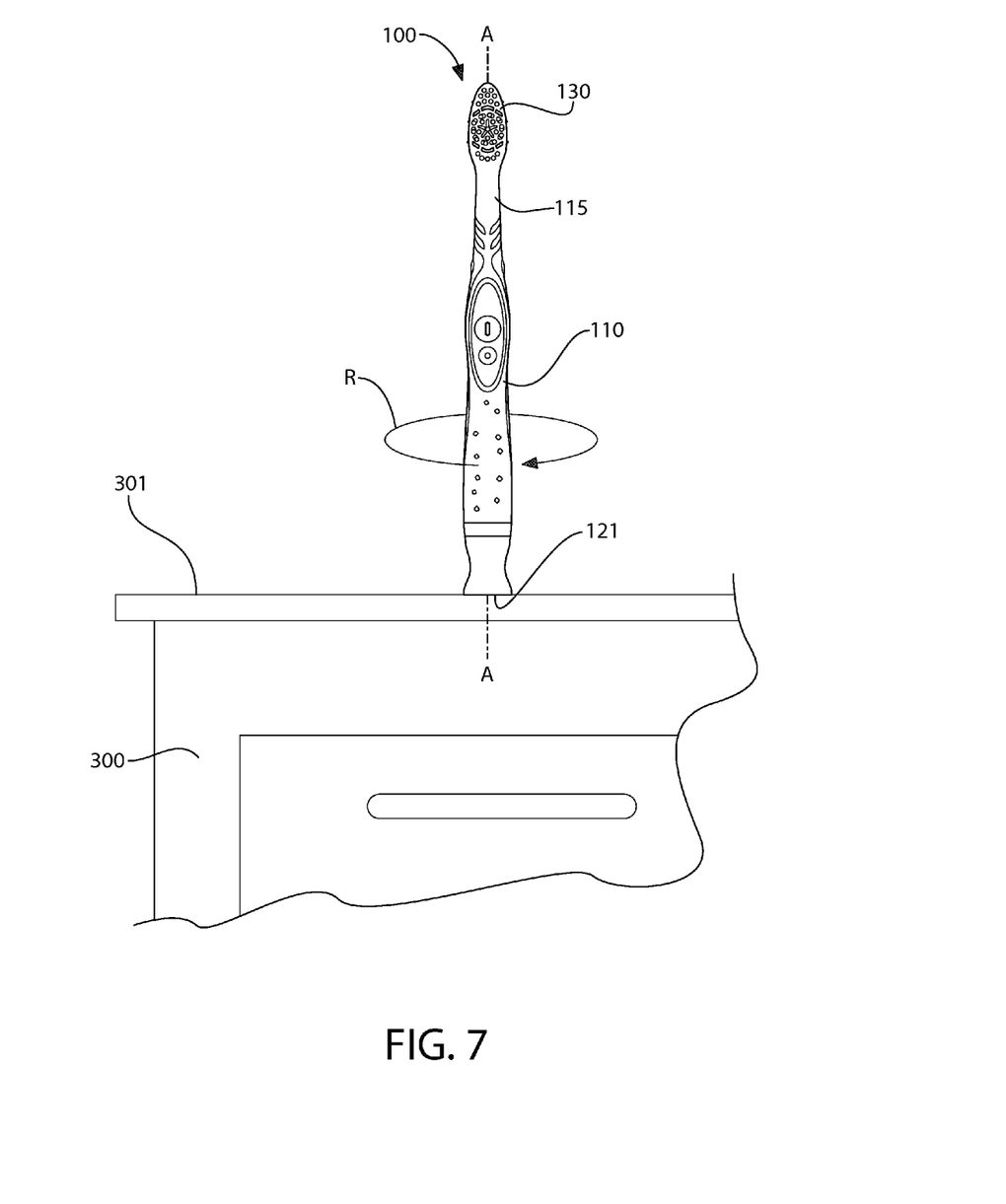
FIG. 7 is a front view of the oral care implement of FIG. 1 standing in a self-supporting upright orientation on a substantially horizontal flat surface and schematically illustrating rotation of the oral care implement.

Referring now to FIG. 7, the toothbrush 100 is illustrated to be standing on a desk 300 having a substantially horizontal flat surface 301. Although the toothbrush 100 is illustrated on the desk 300, the invention is not so limited and the toothbrush 100 can be positioned on any object or apparatus that has a substantially flat horizontal surface. The toothbrush 100 is positioned so that the flat base surface 121 is in surface contact with the substantially horizontal flat surface 301 of the desk 300. When so positioned, the flat base surface 121 of the toothbrush 100, which is perpendicular to the longitudinal axis A-A of the handle 110 in the exemplified embodiment, supports the toothbrush 100 so that the toothbrush 100 can stand in a self-supporting upright orientation on the substantially horizontal flat surface 301 of the desk 300.

When the toothbrush 100 is positioned in the self-supporting orientation (illustrated in FIG. 7) and the mechanical vibratory device 170 is activated, the toothbrush 100 will automatically rotate as shown by the arrow R about the longitudinal axis A-A while maintaining the self-supporting upright orientation. In some embodiments, such as when the substantially horizontal flat surface 301 is a finished wood surface or other similarly finished smooth hard surface, the toothbrush 100 rotates at a rate of between about 20 and about 60 revolutions per minute, more particularly between about 30 and about 50 revolutions per minute, and even more particularly between about 39 and about 45 revolutions per minute.

In certain embodiments, when the toothbrush 100 is positioned in the self-supporting upright orientation and the mechanical vibratory device 170 is activated, the toothbrush 100 concurrently rotates about the longitudinal axis A-A and translates along the substantially horizontal flat surface 301. In other words, the toothbrush 100 may translate across the substantially horizontal flat surface 301 in addition to rotating about the longitudinal axis A-A of the handle 110.

The rotation and/or translation of the toothbrush 100 gives an appearance as if the toothbrush 100 is dancing or twirling on the horizontal flat surface 301. Thus, the toothbrush 100 can be used to provide entertainment to a user prior to or after use of the toothbrush 100.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

While the foregoing description and drawings represent the exemplary embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, sizes, and with other elements, materials, and components, without departing from the spirit or essential characteristics thereof. One skilled in the art will appreciate that the invention may be used with many modifications of structure, arrangement, proportions, sizes, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being defined by the appended claims, and not limited to the foregoing description or embodiments.

What is claimed is:

1. An oral care implement comprising:
   a head comprising a front surface;
   a plurality of bristles extending from the front surface of the head, the front surface of the head disposed within a reference plane;
   a handle extending along a longitudinal axis, a proximal end of the handle comprising a flat base surface;
   a mechanical vibratory device operatively connected to an electric power source, the mechanical vibratory device comprising an eccentric rotatable about a rotational axis to impart vibration to the head when the mechanical vibratory device is activated;
   wherein the head is offset from the longitudinal axis of the handle and extends along an axis that is parallel to the longitudinal axis of the handle;
   wherein the flat base surface is oriented relative to the longitudinal axis of the handle so that the oral care implement can stand in a self-supporting upright orientation on a substantially horizontal flat surface,
   wherein when the oral care implement stands in the self-supporting upright orientation and the mechanical vibratory device is activated, the oral care implement rotates about the longitudinal axis while maintaining the self-supporting upright orientation; and
   wherein the rotational axis is inclined relative to the reference plane so that the eccentric diverges from the reference plane with increased distance from the proximal end of the handle.

2. The oral care implement according to claim 1 further comprising a neck connecting the head to a distal end of the handle, and wherein the mechanical vibratory device is positioned in the neck.

3. The oral care implement according to claim 2 wherein the neck extends along a longitudinal axis that is inclined relative to the longitudinal axis of the handle.

4. The oral care implement according to claim 1 wherein the eccentric is offset from the longitudinal axis of the handle.

5. The oral care implement according to claim 1 wherein when the oral care implement stands in the self-supporting upright orientation and the mechanical vibratory device is activated, the oral care implement rotates about the longitudinal axis while maintaining the self-supporting upright orientation and translates along the substantially horizontal flat surface.

6. The oral care implement according to claim 1 wherein the handle comprises an elongated gripping portion and a base portion detachably coupled to the elongated gripping portion, the base portion comprising the flat base surface.

7. The oral care implement according to claim 6 wherein the electric power source is a battery located in the handle, the base portion comprising an electrical lead that abuts against a pole of the battery when the base portion is attached to the elongated gripping portion of the handle.

8. The oral care implement according to claim 6 wherein the base portion comprises a waist having a transverse cross-sectional area that is less than a transverse cross-sectional area of the flat base surface.

9. The oral care implement according to claim 6 wherein the flat base surface has a first diameter, and wherein a bottom end of the elongated gripping portion has a second diameter that is substantially equal to the first diameter.

10. The oral care implement according to claim 1 wherein when the oral care implement stands in the self-supporting upright orientation and the mechanical vibratory device is activated, the oral care implement rotates at a rate of between about 20 and about 60 revolutions per minute.

11. An oral care implement comprising:
a head comprising a front surface;
a plurality of bristles extending from the front surface of the head, the front surface of the head disposed within a reference plane;
a handle extending along a longitudinal axis and having a flat base surface;
a mechanical vibratory device operatively connected to an electric power source, the mechanical vibratory device comprising an eccentric rotatable about a rotational axis to impart movement to the head when the mechanical vibratory device is activated;
wherein the head is offset from the longitudinal axis of the handle and extends along an axis that is parallel to the longitudinal axis of the handle;
wherein the flat base surface is oriented relative to the longitudinal axis of the handle so that the oral care implement can stand in a self-supporting upright orientation on a substantially horizontal flat surface, and wherein when the oral care implement stands in the self-supporting upright orientation and the mechanical vibratory device is activated, the oral care implement rotates about the longitudinal axis while maintaining the self-supporting upright orientation; and
wherein the rotational axis is inclined relative to the reference plane.

12. The oral care implement according to claim 11 wherein the movement imparted to the head is a vibrational movement.

13. The oral care implement according to claim 11 further comprising a neck disposed between and connecting the handle to the head, the mechanical vibratory device positioned in the neck.

14. The oral care implement according to claim 13 wherein the neck extends along a longitudinal axis that is inclined relative to the longitudinal axis of the handle.

15. The oral care implement according to claim 14 wherein the eccentric is offset from the longitudinal axis of the handle.

16. The oral care implement according to claim 11 wherein the eccentric is offset from the longitudinal axis of the handle.

17. The oral care implement according to claim 11 wherein when the oral care implement stands in the self-supporting upright orientation and the mechanical vibratory device is activated, the oral care implement rotates about the longitudinal axis while maintaining the self-supporting upright orientation and translates along the substantially horizontal flat surface.

18. The oral care implement according to claim 11 wherein the handle comprises an elongated gripping portion and a base portion detachably coupled to the elongated gripping portion, the base portion comprising the flat base surface.

19. The oral care implement according to claim 18 wherein the electric power source is a battery located in the handle, the base portion comprising an electrical lead that abuts against a pole of the battery when the base portion is attached to the elongated gripping portion of the handle.

20. The oral care implement according to claim 18 wherein the flat base surface has a first diameter, and wherein a bottom end of the elongated gripping portion has a second diameter that is substantially equal to the first diameter.

21. The oral care implement according to claim 11 wherein the base portion comprises a waist having a transverse cross-sectional area that is less than a transverse cross-sectional area of the flat base surface.

22. The oral care implement according to claim 11 wherein when the oral care implement stands in the self-supporting upright orientation and the mechanical vibratory device is activated, the oral care implement rotates at a rate of between about 20 and about 60 revolutions per minute.

23. An oral care implement comprising:
a head having a front surface;
a plurality of bristles extending from the front surface of the head in a first direction;
a handle extending along a longitudinal axis, a proximal end of the handle comprising a flat base surface;
a neck connecting the head to a distal end of the handle, the neck extending along a longitudinal axis that is inclined relative to the longitudinal axis of the handle;
a mechanical vibratory device located in the neck and operatively connected to an electric power source located in the handle, the mechanical vibratory device comprising an eccentric that imparts vibration to the head when the mechanical vibratory device is activated, the eccentric inclined in a second direction that is opposite the first direction moving from a proximal end of the eccentric to a distal end of the eccentric;
wherein the head is offset from the longitudinal axis of the handle and extends along an axis that is parallel to the longitudinal axis of the handle; and
wherein the flat base surface is oriented relative to the longitudinal axis of the handle so that the oral care implement can stand in a self-supporting upright orientation on a substantially horizontal flat surface.

* * * * *